US006528092B2

(12) United States Patent
Mullen (10) Patent No.: US 6,528,092 B2
(45) Date of Patent: *Mar. 4, 2003

(54) SYNTHETIC MEMBRANES AND MICELLE-LIKE STRUCTURES COMPRISING LIPO-GLYCOPROTEIN MEMBRANES

(76) Inventor: Elaine H. Mullen, 6733 W. Wakefield Dr., B2, Alexandria, VA (US) 22307

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/372,644

(22) Filed: Aug. 12, 1999

(65) Prior Publication Data

US 2002/0048604 A1 Apr. 25, 2002

Related U.S. Application Data

(63) Continuation-in-part of application No. 08/280,520, filed on Jul. 26, 1994, now abandoned.

(51) Int. Cl.$^7$ .................. A61K 9/107; A61K 9/127; A61K 7/00
(52) U.S. Cl. .................. 424/489; 424/490; 424/491; 424/401; 424/405; 424/417; 264/4.1; 264/4.3; 264/4.6; 514/937

(58) Field of Search .................. 424/450, 1.21, 424/9.321, 9.51, 417, 94.3, 812, 401, 405, 489, 490, 491; 436/829; 514/937–943; 264/4.1, 4.3, 4.6

(56) References Cited

U.S. PATENT DOCUMENTS 5,071,964 A * 12/1991 Dustin .................. 530/395
5,141,751 A * 8/1992 Tomikawa .................. 426/450
5,292,499 A * 3/1994 Evans .................. 424/45

* cited by examiner

Primary Examiner—Gollamudi S. Kishore
(74) Attorney, Agent, or Firm—Browdy and Neimark, P.L.L.C.

(57) ABSTRACT

Synthetic membranes, micelles and vesicles are formed in response to the spontaneous orientation of hydrophobic and hydrophilic groups in aqueous media. The oligosaccharide moieties of glycoprotein molecules are oriented toward the aqueous environment. The micelles of the present invention are relatively stable in aqueous environments, and thus are useful for transporting substances that can be dissolved or suspended in lipids for inclusion in the micelles. Lipoglycoprotein micelles are also useful for protecting substances contained within the hydrophobic compartment from dispersal or degradation until the micelle structure is disrupted.

9 Claims, 4 Drawing Sheets

FIG. 1

MEMBRANE FORMATION

- 10 NON-POLAR LIQUID FLOATS ON SURFACE
- 11 MEMBRANE
- 12 AQUEOUS SOLUTION CONTAINING GLYCOPROTEIN

FIG. 2

MEMBRANE VESICULATES WHEN AGITATED

21 VESICLES AND MICELLE-LIKE STRUCTURES

AGITATION

FIG. 3

FORMATION OF DOUBLE MEMBRANE

GLYCOPROTEIN SOLUTION
INTRODUCED ABOVE MEMBRANE

FIG. 4

MICROSCOPIC VIEW OF MEMBRANE DEVOID
OF SOLVENT

PARALLEL STRIATIONS
ABOUT 2.5 μ APART

FIG. 5

FIG. 6

SYNTHETIC MEMBRANES AND MICELLE-LIKE STRUCTURES COMPRISING LIPO-GLYCOPROTEIN MEMBRANES

CROSS-REFERENCE TO RELATED APPLICATIONS

The present application is a continuation in part of application Ser. No. 08/280,520, filed Jul. 26, 1994, now abandoned, the entire contents of which are hereby incorporated by reference.

FIELD OF THE INVENTION

The present invention relates to synthetic membranes, micelles, and vesicles.

BACKGROUND OF THE INVENTION

In living plant and animal cells, non-polar lipids are stored in droplets within the cytoplasm and are rarely found in biological membranes. Proteins which have been isolated from membranes of living cells often possess a sequence of non-polar amino acids which anchor the proteins through hydrophobic associations within the interior of phospholipid bilayers. Other proteins are anchored through covalent bonds to glycophospholipids. The oligosaccharide moieties of membrane glycoproteins and glycophospholipids project into the aqueous environment.

Phospholipid monolayers and bilayers form micelles and liposomes which have been used successfully in delivering pharmaceutical agents. However, the chemical and mechanical instablity of these constructs have posed problems. Liposomes are prone to oxidation and tend to aggregate and fuse during prolonged storage. Injected liposomes are degraded by the lecithin-cholesterol acyl transferase of high density lipoproteins, and are cleared from the bloodstream by macrophages and hepatocytes. Though it is possible to attach certain glycoproteins to phospholipid micelles, polar phosphate heads facing the aqueous solution tend to inhibit contact of lipid tails with the hydrophobic amino acids of glycoproteins.

Both amino acid sequences and oligosaccharide segments of glycoproteins can contribute chemical and biological properties that may be useful components of drug delivery agents. Glycans present on the exterior surfaces of lipo-glycoprotein vesicles and micelles may be useful for protecting ingested therapeutic and nutritional substances against chemical degradation in the gastrointestinal tract. For instance, Gu et al. demonstrated the role of oligosaccharide moieties in protecting ovomucoid, a glycoprotein found in hen egg whites, against tryptic hydrolysis and heat denaturation.

Sialic acid, the terminal sugar of many oilgosaccharides produced in animal tissues, is ionized at pH 7 (Lehninger et al., 1993). Its presence inhibits uptake and degradation by hepatocytes of circulating blood cells and glycoproteins. Baenziger et al. discovered in 1992 that terminal sulfated oligosaccharides also prevent hepatocyte clearance from the circulation. The presence on micellar surfaces of glycoproteins bearing terminal sialic acid or sulfated glycans may thus prevent or delay uptake by the liver and phagocytic blood cells of therapeutic agents injected into the bloodstream.

Micelles are aggregates of substances in which hydrophilic polar groups of compounds orient themselves toward and interact with the aqueous phase. The hydrophobic nonpolar hydrocarbon chains of the micelles are hidden within the structure. For example, micelles which contain soap molecules remain evenly suspended in water because their surfaces are negatively charged and the micelles repel each other. Micelles prepared from phospholipids and oligosaccharide-lipid complexes have been used to prepare vaccines using natural and synthetic oligosaccharides, which are immunogens, to prepare stabilized vaccines, disclosed in U.S. Pat. No. 5,034,519, the entire contents of which are hereby incorporated by reference.

It is also known that amphipathic proteins such as cytochromic oxidase, an intrinsic enzyme found in mitochondrial membranes, when placed in suspension with lipids form sac-like vesicles that are, in effect, man-made membranes. These vesicles have been used as model systems for the study of the isolated protein's relationship with lipid bilayers.

Compans, U.S. Pat. No. 4,790,987, teaches the preparation of viral glycoprotein subunit vaccine by complexing a lipid with the glycoprotein. Compans also teaches that the complexes can be obtained by dissolving a lipid in a dialyzable detergent solution containing glycoproteins, then dialyzing the solution to obtain the protein-lipid complex. The lipids are phospholipids. The resulting complexes are then administered in pharmaceutically acceptable carriers.

Rutter et al., in U.S. Pat. No. 4,769,238, note that vaccine bound to a membrane may be superior to non-membrane bound proteins.

Mouritsen et al. have studied protein-protein and protein-lipid interactions in phospholipid bilayers in an attempt to refine the fluid mosaic model of biomembranes proposed in 1972 by Singer-Nicolson. In 1995 Oin et al. produced two-dimensional crystals of avidin on the hydrophobic surface of a phospholipid monolayer. In both synthetic and biological phospholipid membranes, polar heads of component molecules lie adjacent to one another at the aqueous interface, shielding their hydrophobic lipid tails from contact with water or molecules dissolved therein.

Unger et al., in U.S. Pat. No. 5,853,752, described methods of preparing gas-filled phospholipid microspheres to act as contrast agents in ultrasound image formation. Feinstein, in U.S. Pat. Nos. 4,718,433 and 4,774,958, teaches the use of albumin-coated microbubbles for the same purpose. These technologies exploit the changes in acoustic impedance that occur as sound waves encounter interfaces between solids, liquids, and gases. The greater the elasticity of this interface, the more efficient the reflection of sound. Changes in acoustic impedance result in a more intense signal in the ultrasound image.

In U.S. Pat. No. 5,846,744, Athey et al. describe a novel sensor format based on the impedance analysis of polymer coatings on electrodes for determining the presence or amounts of an analyte in a sample of assay medium.

SUMMARY OF THE INVENTION

It is an object of the present invention to overcome the aforesaid deficiencies in the prior art.

It is another object of the present invention to provide micelles and vesicles which can be used for transporting substances that can be dissolved or suspended in lipids.

It is a further object of the present invention to extract glycoproteins from solution.

The present invention provides synthetic membranes, micelles and vesicles that form in response to the spontaneous orientation of hydrophobic and hydrophilic groups in aqueous media. Unlike phospholipid monolayers, micelles, and liposomes, the membranes of the present invention comprise a sheet of glycoprotein molecules associated on one face with a non-polar liquid, and on the other face with water. The oligosaccharide moieties of glycoprotein molecules are oriented toward the aqueous environment.

The micelles of the present invention are relatively stable in aqueous environments, and thus are useful for transporting substances that can be dissolved or suspended in lipids for inclusion in the micelles. Lipo-glycoprotein micelles are also useful for protecting substances contained within the hydrophobic compartment from dispersal or degradation until the micelle structure is disrupted.

Certain glycoproteins incorporated into the membranes of micelles according to the present invention may limit the first pass effects of drugs contained within the hydrophobic compartment by resisting chemical degradation in the stomach or other segment of the gastrointestinal tract through which they pass. Other glycoprotein components of micelles employed in the delivery of injected drugs may serve as signals for inducing or inhibiting their uptake by cells of certain tissues. Still other glycoproteins contain amino acid sequences or segments of oligosaccharide moieties that are bioactive and may be used as therapeutic agents. Micelles of the present invention can also be used for delivering such glycoproteins. For instance, oligosaccharide components of a membrane may confer to drug delivery agents properties such as cellular recognition signals. It is also possible to include two or more species of glycoprotein with differing biological activity on a single micelle. In addition, membrane surface characteristics and micellar diameter can be used to prevent the movement in the body of bound glycoprotein from one fluid compartment to another.

Lipo-glycoprotein membrane formation can be used to extract both glycoproteins and oils from aqueous solution. During the process of membrane formation, strong intermolecular attraction traps glycoproteins and hydrophobic liquids. Very small concentrations of glycoprotein and oil can be collected in membranes and removed mechanically from the surface of an aqueous solution. Volatile organic liquids are sequestered within micelles that form when the membrane is agitated.

Membrane formation can also be employed in sensor design. For example, an oil-filled tube having a small aperture can be inserted into an aqueous solution, then withdrawn and subjected to measurement of light absorption or penetration through the aperture to detect proteins present therein. To sense the escape of organic solvents from an industrial process, a cool sample can be introduced into an aqueous solution of glycoprotein and agitated. The formation of micelles at the surface would not only indicate the presence of hydrophobic chemicals, but would facilitate their recovery.

Membranes or micelles bearing glycoprotein antigens or antibodies can also be used to extract target molecules from aqueous samples of solutions containing tissue fluids or disease-causing organisms. Sensors employing this method might be useful in the inspection of foods and in forensic science. Filters made of cellulose or synthetic fibers coated with lipo-glycoprotein membranes bearing antibodies might also be used to remove certain organisms or biotoxins from aqueous solution. Enzymes can be incorporated into the micelles of the present invention to catalyze a variety of chemical reactions in aqueous media.

Hydrated glycans are preserved on membrane surfaces and can be studied in situ. The association of lipid with glycoproteins appears to maintain the orientation of carbohydrate moieties and facilitate the rehydration of dried micelles. Oligosaccharide components prevent aggregation and fusion of micelles and inhibit their degradation by heat and protease.

Stable glycoprotein membranes are prepared by first layering a non-polar liquid on top of an aqueous mixture containing at least one glycoprotein or proteoglycan. A membrane then forms at the aqueous-non-polar interface site. When agitated, said membrane breaks apart into vesicles and micelles having an oligosaccharide surface facing the aqueous solution and enclosing one or more hydrophobic substances. Gentle agitation of the membrane produces vesicles of sufficiently large diameter to permit easy removal from the aqueous solution in which they are disposed. The large vesicles may then be passed through a strainer or screen to divide them into smaller micelles. Micelles produced by association of non-polar liquids with glycoproteins are mechanically and chemically more stable than those derived from phospholipids.

An inverse micelle may be produced by introducing a droplet of aqueous solution containing glycoprotein into a non-polar liquid such as olive oil. The glycoprotein forms a membrane around the aqueous solution, creating a vesicle having a hydrophobic exterior surface. Inverse micelles introduced into the lipid layer floating above a lipo-glycoprotein membrane will be enclosed within the hydrophobic compartment when the membrane is agitated to form closed vesicles.

BRIEF DESCRIPTION OF THE DRAWINGS

FIG. 1 illustrates membrane formation according to the present invention.

FIG. 2 shows how membrane brakes into vesicles and micelle-like structures.

FIG. 3 shows formation of a double membrane.

FIG. 4 illustrates the microscopic structure of hexane-glycoprotein membrane.

FIG. 5 shows how glycoprotein is recovered from water.

FIG. 6 illustrates trapping carbon dioxide.

DETAILED DESCRIPTION OF THE INVENTION

The structures of the present invention are based upon the discovery that many glycoproteins present in plant and animal tissue fluids spontaneously aggregate at the interface between certain aqueous solutions and certain non-polar liquids to form a flexible membrane. Lipophilic components of glycoproteins adhere, through non-covalent hydrophobic interactions, to molecules of oil, and present their hydrophilic moieties toward the aqueous phase to produce a membrane that is mechanically and chemically more stable than those made from phospholipids. This phenomenon of spontaneous lipo-glycoprotein membrane formation can be used to detect the presence of certain proteins and hydrophobic substances, and to filter or sequester them for removal from solution. Additional substances can be introduced to the lipid surface of a membrane. Vesicles and micelle-like structures which form upon subsequent agitation will enclose and protect these substances for delivery in foods, drugs, flavorings, coloring agents, and cosmetics. An emulsion containing hydrophilic substances can also be included within micelles of the invention for use in controlled or sustained drug delivery. Oligosaccharides also confer resistance to protease and control the half-life of particulates circulating in the bloodstream.

Through the process of membrane formation, trace concentrations of glycoprotein can be collected from aqueous media in order to study oligosaccharide moieties contained therein. The presence of oil floating on a solution of glycoprotein causes molecules to align so that oligosaccharides project into the aqueous solution. oligosaccharide moieties can be enzymatically removed from a lipo-glycoprotein membrane, or subjected to study in situ.

Glycoproteins that are stored on the surfaces of oil-filled micelles can often be dried and then rehydrated. However, dried membranes lose their elasticity and are fragile. When volatile hydrocarbons are used to induce membrane formation, evaporation of organic and aqueous solvents leaves behind a diaphanous, brittle monolayer of glycoprotein. The structure of these delicate membranes can be studied using methods such as X-ray crystallography and electron microscopy to provide insight into protein-protein interactions.

The micelles of the present invention can also be used to isolate native glycoproteins extracted from plant and animal tissue fluids using micellar electrokinetic chromatography. The micelles of this invention can also be used as imaging agents, growth media, and components of microelectronic systems. Formation and degradation of lipo-glycoprotein membrane may also be used in sensor technology to indicate the presence of certain chemicals and microorganisms in aqueous environments.

Membranes according to the present invention are prepared by:

(1) layering a non-polar liquid on top of an aqueous mixture containing at least one glycoprotein or proteoglycan and (2) allowing a membrane to form at the interface between the aqueous and hydrophobic liquids.

Lipophilic substances added to the hydrophobic surface of the membrane may be enclosed within vesicles or micelles when the membrane is agitated. However, water and other polar substances introduced on the surface will penetrate the membrane and enter the aqueous phase below. It is interesting to note that a membrane may spontaneously mend the opening made by a water droplet. Droplets of aqueous solution disbursed within the oil compartment of a micelle will eventually escape. Protein gels and boiled starch can be used to stabilize polar substances contained within the hydrophobic compartment of lipo-glycoprotein micelles.

FIG. 1 illustrates formation of membranes for making micelles according to the present invention. When a non-polar liquid 10 such as a lipid or saturated hydrocarbon is layered on the surface of an aqueous solution 12 containing glycoprotein, a membrane 11 forms at the interface. Additional hydrophobic substances can be added to the surface of the membrane.

When a lipo-glycoprotein membrane is rolled, shaken, or forced through a filter, it stretches and breaks into closed vesicles or micelles. Large vesicles formed by gently agitating a membrane can often be lifted from solution on mesh with openings as large as 1.25 mm. Smaller micelles may be obtained by pouring the micelles through smaller mesh, by multiple passages through the mesh, or by increasing the pressure under which the liquid containing the micelles is forced through the mesh. Nylon filters having pores of 0.2 mm have been particularly useful for breaking large vesicles into smaller units ranging from about 1 to 5 microns in diameter. Pouring the mixture between two containers also produces smaller and smaller micelles as the process is repeated. Solutions containing large numbers of micelles having diameters between 2.5 microns and 1 micron have been obtained by using atomizers to produce a mist of glycoprotein into which oil is sprayed. Because metallic residues are absorbed by certain glycoproteins from stainless steel, nylon filters and glass or plastic containers are preferred for breaking up the membranes.

FIG. 2 shows that, when agitated, the membrane 11 of FIG. 1 breaks into large vesicles 21 and micelle-like structures 21.

In a freshly prepared aqueous solution, oil-filled micelles can be seen rising at widely varying rates proportional to the diameter of the micelles. Larger micelles contain a relatively greater amount of oil and rise more quickly to the top of the solution. When the preparation is transferred to a test tube, this phenomenon is easily observed through a hand-held lens. During the first three hours, the density differential produces a clear vertical separation of micelles greater than 10 microns in diameter. If a second aqueous solution is carefully added to the top of the first, larger micelles will rise through it, while microscopic micelles between 1 and 10 microns remain suspended in the original solution and may be extracted therefrom. At the surface, the largest vesicles are intercalated among smaller micelles. Laminar flow and attraction of micelles to glass walls can cause errors in separation when tubes narrower than ¼ inch are used.

Larger micelles containing materials which are more dense than oil will float in a layer containing smaller oil-filled micelles. Vertical separation can thus be used to distinguish micelles by the density of the contents thereof. Once a layer has been selectively extracted, the micelles can be separated by size exclusion.

A drop of aqueous solution containing glycoprotein, when introduced into a lipid floating above a glycoprotein membrane, will form a second membrane. This membrane-bound vesicle, with its hydrophobic face oriented toward the exterior, is essentially an "inverse" or "reverse" micelle. By virtue of its weight relative to oil, a large droplet will sink down, suspended by the original membrane, into the aqueous phase. With agitation, the droplet will stretch and break free of the surface membrane, completely enclosed within a double membrane. Sometimes a small oil-filled tube connects the outer glycoprotein envelope to the surface membrane from which it was derived.

FIG. 3 shows formation of a double membrane. Inverse micelles 31 can be added to or formed in the hydrophobic liquid is 32 above the membrane 34. These micelles could include inverse phospholipid micelles which contain a hydrophilic drug. The compound vesicles so formed have a double membrane. The hydrophobic surfaces of the membranes eventually fuse, which makes these useful for delayed release of drugs.

Hydrophilic substances sprayed or dusted onto the surface of an oil emulsion of glycoprotein solution will tend to enter the microscopic inverse micelles. When such a preparation is added to a second glycoprotein solution and agitated, a mixture of liposome-like vesicles is prepared. If more than one inverse micelle is contained within a single vesicle, the non-polar faces of their membranes sometimes fuse. By the same mechanism, membranes of microscopic inverse micelles eventually become confluent with the bounding membrane and expel their aqueous contents into the surrounding environment.

Preparations of oil-filled micelles containing smaller inverse micelles sequestering a solution of glycoproteins have been stored, capped with oil, at room temperature for weeks. It is interesting to note that membranes of inverse micelles often appear wrinkled and flaccid compared to those of bounding micelles, indicating that water has escaped. Small tubes have occasionally been seen connecting the membrane of an inverse micelle with that of the bounding membrane, establishing continuity between the inner aqueous compartment and the environment.

Figure 1:
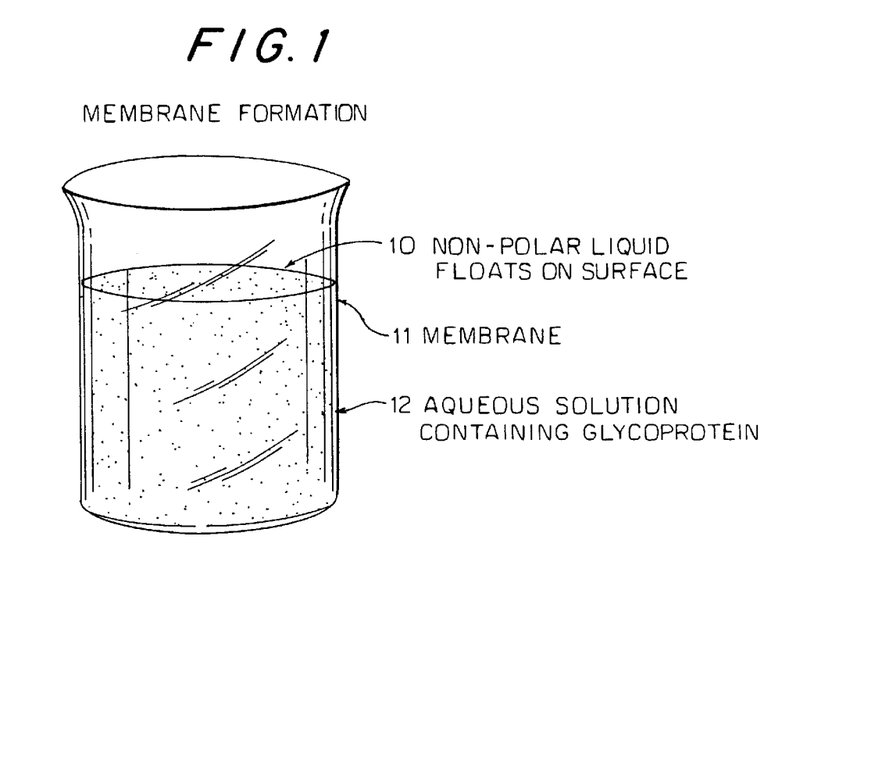
Figure 2:
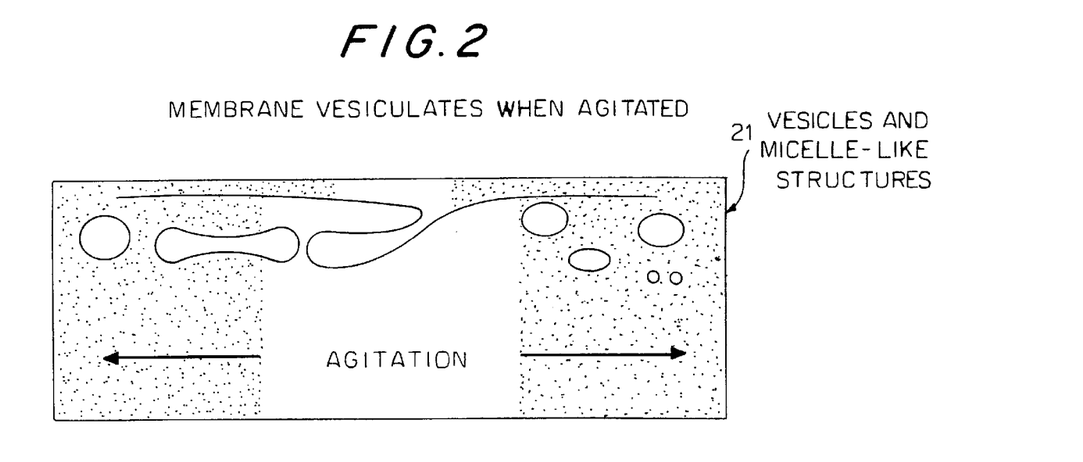
Figure 3:
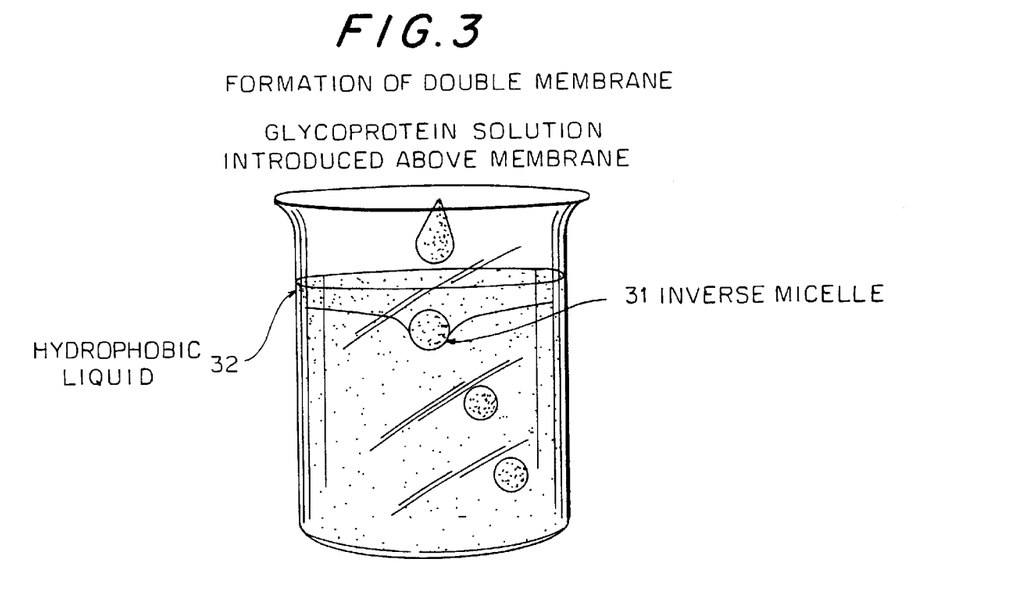
Figure 4:
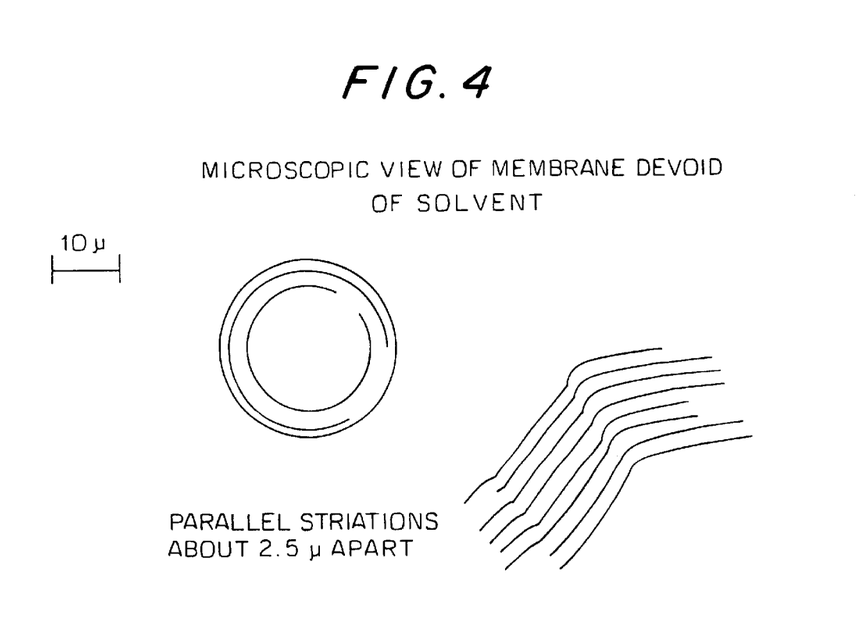

When micelles are formed in a hydrocarbon liquid such as hexane or heptane, the micelles tend to stick together and occasionally float in the hexane layer. This indicates a different surface configuration from that of lipid-filled micelles, which float in the aqueous layer after formation. Heat or slight vacuum ruptures micelles containing hexane or heptane, leaving a fragile glycoprotein membrane on the substrate. Microscopic examination of a membrane formed from hexane and ovomucoid reveals parallel striations about 2.5 microns apart. This is illustrated in FIG. 4.

Figure 5:
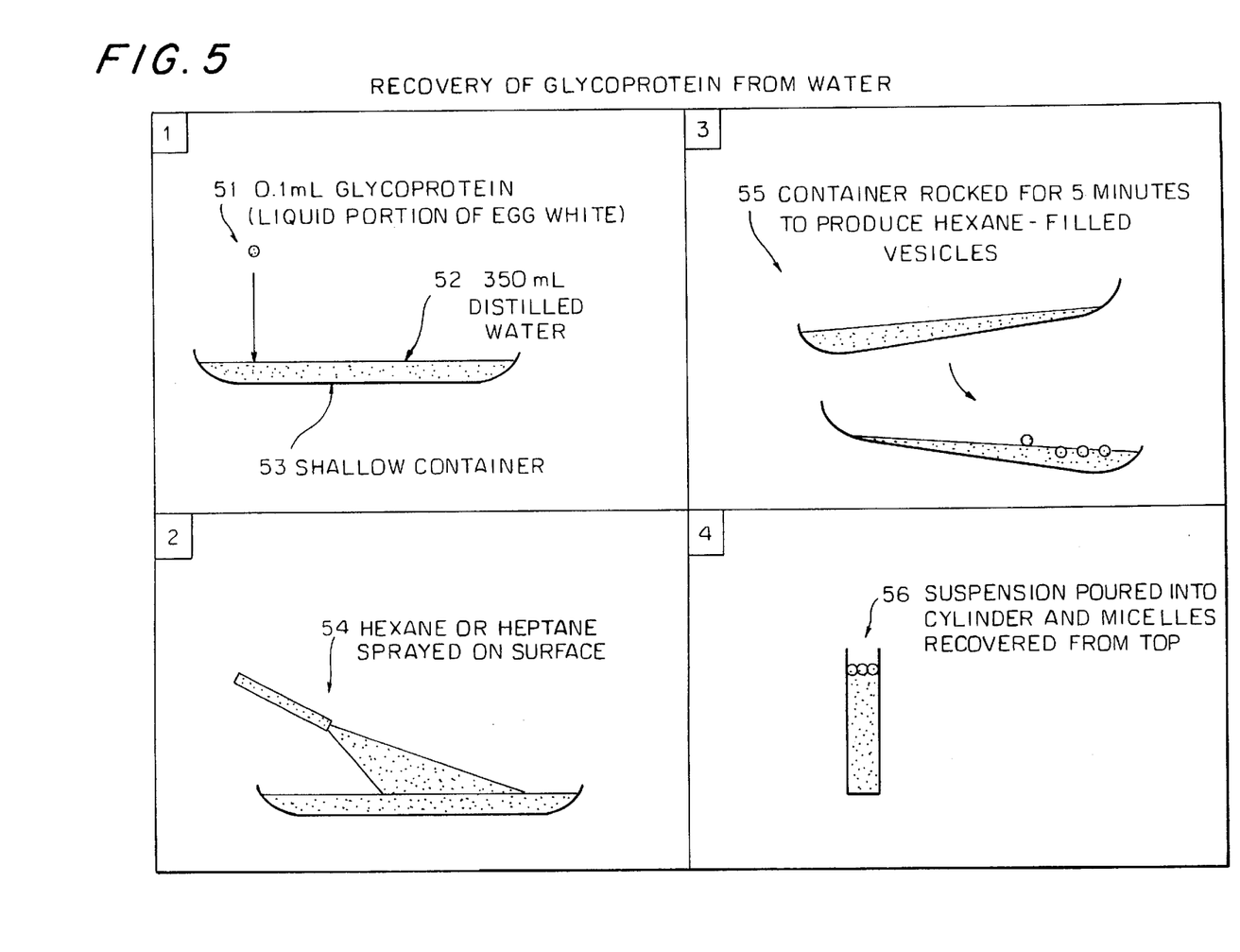

FIG. 5 shows recovery of glycoprotein from water. In the first frame, glycoprotein, ovomucoid from egg white 51 is added to distilled water 52 in a container 53. Next, hexane or heptane is sprayed onto the surface of the water 54. The container 55 is then rocked for about five minutes to produce hexane-filled vesicles. This suspension is poured into a cylinder 56 The micelles so formed 56 are recovered from the top of the cylinder.

Figure 6:
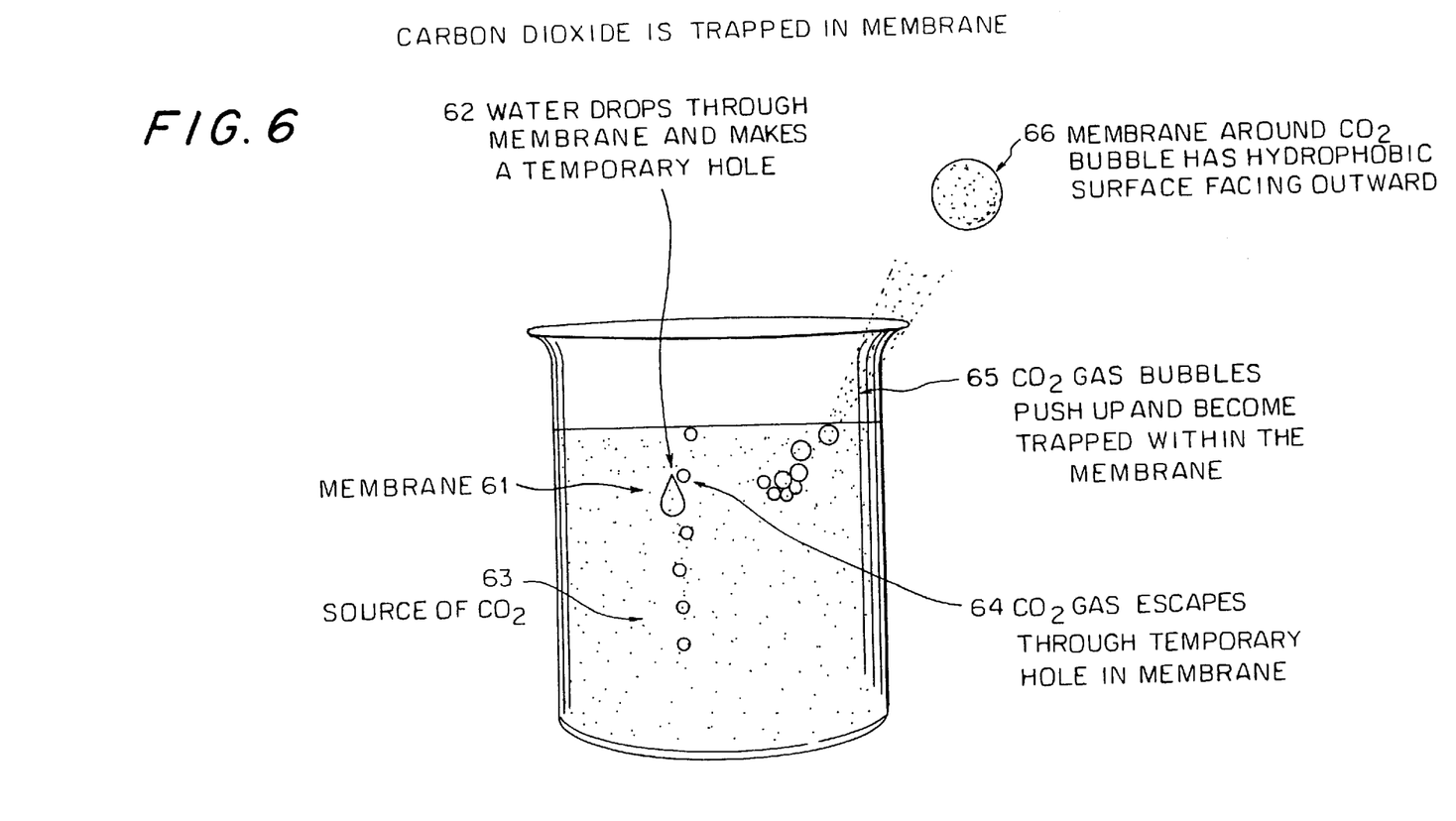

As illustrated in FIG. 6, carbon dioxide can be trapped in the micelles of the present invention. First, a membrane 61 is formed on top of a source of $CO_2$ 63. Water is dropped through the membrane and makes a temporary hole 62 through which $CO_2$ gas 64 escapes. Carbon dioxide bubbles push up and become trapped within the membrane 65. The gas does not escape through the intact membrane. The membrane around the $CO_2$ bubble 66 has its hydrophobic surface facing outward. When the bubble is punctured, the membrane persists even after the $CO_2$ escapes.

The micelles of the present invention are capable of trapping volatile substances therein. For example, diallyl disulfide (garlic oil) can be trapped within glycoprotein micelles by forming the membrane before the garlic oil is added. Likewise, hexane can be trapped in a membrane and stored over water in open containers. These membranes can be used to trap volatile substances used to detect illegal drugs, train animals, etc.

The lipo-glycoprotein membranes of the present invention are stretchy and self-mending if broken. They can be forced repeatedly through fine mesh to produce progressively smaller micelles. It was found that robust micelles made from proteoglycans are weakened by forcing through fine mesh, presumably because oligosaccharides and mucopolysaccharides, which appear to confer mechanical and chemical stability to the membrane, have been removed.

Many of the micelles formed according to the present invention can be kept for months at room temperature in sterile aqueous solution.

Microbes present in aqueous solution occasionally cause the membranes to fuse. Although lipo-glycoprotein membranes can be boiled, the oligosaccharides may be removed.

The lipo-glycoprotein membranes are relatively stable chemically. The micelles do not break down when acids, bases, or surfactants are added to a liquid containing these micelles. However, alcohols can penetrate micellar membranes and change the properties of constituent molecules.

The strength of the membranes depends on the particular lipids and glycoproteins used to prepare the membranes. Certain chemicals disrupt or prevent formation of lipoglycoprotein membranes. For example, both diallyl disulfide and flax seed oil not only interfere with membrane production they also disrupt otherwise stable membranes formed from olive oil and egg white glycoproteins. All of the lipo-glycoprotein membranes tested thus far are degraded by proteases in basic solution, although some of the membranes were more resistant than others.

Micelles prepared from membranes according to the present invention can be used to trap, protect, and/or transport substances contained within the interior of the micelles, including nonpolar liquids and gases in polar liquids; polar liquids and gases in nonpolar liquids; pharmaceutical and other drugs, dyes, odorants, reactants, catalysts, fuels, markers, etc.

Organic solvents such as hydrocarbons, lipids, and liquid waxes can be trapped within a membrane and then mechanically separated from the surface of an aqueous solution. Membrane formation is induced by the addition of glycoprotein to the solution. Concomitantly, glycoproteins are extracted from aqueous solution by membrane formation. This is particularly useful for forensic science, purification processes, and sensors. For example, glycoproteins present in plant and animal tissue fluids such as vegetable juice, blood, or saliva can be extracted from an aqueous solution through membrane formation with organic solvents or oils floating on the surface. Membranes and large vesicles can be lifted from the surface of an aqueous medium, washed, and introduced into a second solution. Microscopic micelles can be recovered by centrifugation or by lectin or antibody-antigen reactions.

Carbohydrate moieties of glycoproteins are key components of various intercellular recognition processes. Glycoproteins on the outer surface of the micelle can be chosen to target appropriate tissue, inhibit uptake by tissue, and induce endocytosis of the micelle. Antibodies, apoproteins, and opsonins are examples of glycoproteins that mediate these responses.

Hydrophobic drugs can be enclosed within the lipo-glycoprotein membranes of the present invention. Smaller inverse micelles containing a hydrophilic drug can be kept within the hydrophobic compartment. Fusion of component membranes can be used to release the drug into the bloodstream or the interior of a cell. In addition to delivering pharmaceuticals, the micelles can be used to deliver DNA to the interior of a cell.

Proteins and glycoproteins are pulled from aqueous solution by association with a lipid or hydrocarbon. Membranes or large vesicles can be lifted from the surface of the solution.

Glycoproteins bind with organic solvents suspended in aqueous solution. Microscopic micelles can be recovered through lectin or antibody-antigen reactions with oligosaccharides contained on their surfaces.

While it is not known positively what is the structure of lipo-glycoprotein membranes, it is possible that a β-pleated sheet of hydrogen-bonded protein chains may lie between water and lipid layers. Groups containing oligosaccharides would face the water, while nonpolar groups would be immersed in the lipid layer. The formation and preservation of stable micelles appears to depend on the association of glycoprotein with both oil and water.

Lipo-glycoprotein membranes may be altered by various physical and chemical processes. For example, micelles made with egg white as the source of glycoprotein, when repeatedly passed through small pores, have, thereafter, adhered to each other in aqueous solution. This phenomenon suggests that certain glycans are removed during filtration. Micelles of the invention break down in solutions containing protease. The rate of disruption at a given pH and enzyme concentration depends on the particular glycoproteins and lipids used to prepare the micelles.

Molds and bacteria also alter the lipo-glycoprotein membranes. Removal of oligosaccharides by bacteria introduced into the aqueous phase may cause the micelles to adhere to one another. In the case of membranes made from egg white, unwashed micelles are rarely contaminated by bacteria and may last for months at room temperature in open containers. This phenomenon may be attributed to the presence of lysozyme that is naturally present in egg white.

The characteristic affiliation of molds and bacteria for the oil or aqueous phase of a membrane preparation may provide a means of distinguishing and separating them. Juices from most fruits support water molds that grow in the aqueous phase. However, the mold typically found in grapefruit projects hyphae into the hydrophobic phase, and will even grow in the presence of heptane. Molds found in nuts tend to form a mat of hyphae in the membrane and project a second set upward into the hydrophobic phase. Thus, it may be possible to use a lipo-glycoprotein preparation as a culture medium, and to extract metabolites from the aqueous or hydrophobic phase.

A large shallow dish is useful for exposing the maximum amount of glycoproteins in solution to the surface, and requires the use of more lipid to form a membrane that covers the entire surface. It is possible to effectively distribute a thin layer of lipid or hydrocarbon using an atomizer to spray it over the surface. In most of the experiments described herein, the containers have an inner diameter of about 2.5 inches. About 5 ml lipid is generally used to cover the surface of the aqueous solution containing glycoproteins.

Dehydration of lipo-glycoprotein micelles generally causes the membranes to become brittle. Dry micelles break open and release their contents if subjected to mechanical stress. However, when water is added, intact oil-filled micelles often regain their flexibility. In contrast thereto, volatile non-polar compounds such as hexane tend to escape through brittle membranes of dried micelles. Devoid of both aqueous and non-polar solvent, proteins often self-aggregate and are not readily hydrated.

When isopropanol is added to an aqueous suspension of lipid-filled micelles, the diameters of the micelles change and the membrane surfaces become rough. This phenomenon may indicate that alcohol penetrates the membrane and changes the properties of the component glycoproteins.

The Glycoprotein Component

The term "glycoprotein", as used herein, includes compounds known as mucoproteins and proteoglycans. The classification of glycoproteins has become complicated by recent elucidation of their structures. For example, glycosaminoglycans, once thought to be attached only in O-linkages to serine and threonine side chains, have been detected in N-linkage to asparagine side chains of cell surface glycoproteins (*Oxford Glycosystems, 1994).

The properties of lipo-glycoprotein membranes vary greatly, depending on the nature and condition of component constituents and on methods used in their preparation. Many glycoproteins are fragile and become denatured or altered when exposed to a variety of chemical and physical conditions. For example, some glycoproteins are irreversibly altered by slight changes in salinity or pH. Therefore, certain commonly used laboratory methods and materials must be avoided.

It has been demonstrated that the presence of hydrated oligosaccharide moieties prevents self-aggregation of certain glycoproteins (Scott and Dodd, 1990). This may explain observed changes in solubility of some glycoproteins when they are dehydrated, frozen or exposed to hydrophobic liquids. In general, the glycoproteins mentioned in the examples of this disclosure were obtained from fresh plant and animal tissue fluids.

Once formed, lipo-glycoprotein membranes are often quite resistant to destruction. It is interesting to note that micelles formed from olive oil and the water-miscible portion of egg white are not broken by liquid detergent. Lipo-glycoprotein membranes can be boiled and sterilized by heat for use in foods or pharmaceutical products. However, oligosaccharide moieties are sometimes removed during heating. Proteins devoid of glycans generally do not exhibit hydrophilic properties. Deglycosylated micelles adhere to one another and, when agitated, form complex structures of oil-filled vesicles within bounding membranes. These are similar to structures that form when oil is mixed with ovalbumim and other proteins that tend to self-aggregate. It is interesting to note that glycoprotein membranes devoid of solvent act as a barrier to water but are readily wetted by oil.

Because of its availability, ease of preparation, and known glycoprotein content the liquid portion of fresh, unfertilized hen egg white (about 5 ml fluid per 35 ml egg white) has been used most often to study the formation and properties of lipo-glycoprotein membranes. Tissue fluids from many other animal and plant sources have also been used to produce membranes and micelles. These include extracts from chicken skin and muscle; human saliva, bronchial secretions, and blood; and juices squeezed from oranges, limes, melons, grapes, plums, apples, and onions. However, juices from members of the genus Solanum (nightshade) which includes vegetables such as green bell peppers and tomatoes, have not produced lipo-glycoprotein membranes. It is also interesting to note that, while grapefruit juice often contains glycoprotein that forms a membrane with oil, sometimes it does not.

Ovalbumin is the major component of egg white, and constitutes most of the central portion that surrounds the yolk. Although it binds strongly with triglycerides, and is mono-N-glycosylated (Suzuki, et al., 1997), it does not dissolve sufficiently in normal saline solution or water to form a membrane when oil is added the surface.

If an isotonic solution of NaCl is added to the liquid portion of egg white that surrounds the ovalbumin, no glycoprotein precipitates. However, micelles made from such a preparation are irregular in shape and difficult to break up when forced through a filter with pores of 1.25 mm.

In most of the experiments described in this disclosure 30 ml of steam distilled water is added to about 5 ml of liquid egg white which has been decanted from the ovalbumin and yolk of a fresh hen egg. Certain proteins are denatured and settle to the bottom of the container. Although a nylon filter can be used to remove these from the preparation, it is preferable to use a separation funnel or pipette.

The fluid portion of egg white contains a mixture of glycoproteins bearing multiple N-linked oligosaccharides. Among these are the Kazal-type serine proteinase inhibitors that have been studied extensively during the past 20 years. The amino acid sequences, trypsin-binding sites, and carbohydrate structures of several homologous members of this group are now known (Laskowski and Kato, 1987; Piskarev and Likhosherstov, 1989.)

All N-linked glycans share a common pentasaccharide core to which is attached an enormous variety of oliogosaccharides that vary greatly in complexity. In mammals, the number of antennae attached to the core ranges from two to four. These may be further elaborated by the addition of terminal groups such as sialic acid. However, the avian oviduct synthesizes a variety of pentantennary N-glycans.

Ovomucoid consistently occupies about 10 mg/ml of avian egg white (Laskowski, et al., 1987). Since 1960, it has been used to study the relationship between amino acid sequence and reactivity in serine proteinase inhibition. The carbohydrate chains of ovomucoid are similar in structure to those found in many other glycosylated avian egg proteins. They are characterized by up to six residues of n-acetylglucosamine bound to a pentasaccharide core (Piskarev, et al., 1990.) Ovomucoid has been identified as the major egg allergen and antigen in human beings (Bernhisel-Broadbent, et al., 1994.)

The following glycosylated proteins also exist in hen egg white: ovoinhibitor (Matsushima, 1958), a serine proteinase inhibitor of seven homologous Kazal-type domains that is found in the egg white and blood of birds (Laskowski, et al., 1980); riboflavin-binding glycoprotein (Likosherstov, et al., 1991); ovotransferrin (Piskarev, et al., 1989); lysozyme (Trudel and Asselin, 1995), and the lipocalin protein, avidin (Flower, 1996) (Nardone, et al., 1998).

The tenacious binding of avidin to the vitamin, biotin is widely known. Because avidin also has a strong affinity for certain dyes, strands of it can be seen adhering to the surfaces of micelles. It is interesting to note that membrane-bound avidin continues to bind with biotin, and that dye appears to be displaced during the reaction. Avidin molecules tend to self-aggregate and therefore cause micelles to clump together. Avidin is one of several components of the more fluid portion of egg white that are denatured by distilled water.

Glycoproteins are extracted from the juices of many fruits and vegetables by the addition of oil to the surface. However, membrane formation is often accompanied by the absorption of lipophilic pigments and subcellular components into the oil phase. Although some impurities can be removed through filtration or centrifugation, others include molecules that may interfere with membrane formation or interact with materials later introduced into the lipid.

The Hydrophobic Component

Lipids float on the surface of water for two reasons. Because they are non-polar, lipids are insoluble in water, and do not, alone, form stable emulsions. Secondly, lipids have lower specific gravity than water. Double bonds in the hydrocarbon chains of unsaturated oils produce kinks that prevent crystallization. For this reason, lipids containing unsaturated fatty acids are liquid at room temperature.

Olive, corn, peanut, canola, soybean, and safflower oils have been used in the preparation of stable lipo-glycoprotein membranes and micelles. Olive oil generally produces a more flexible, less stable membrane than that made with corn, soybean, peanut or safflower oils. Lanolin, a wax, has also been found to produce a membrane when layered on a solution containing glycoprotein. However, micelles formed from lanolin and the liquid portion of egg white may not be stored at room temperature for long periods of time.

Certain oils and lipophilic substances present in plant and animal tissues interfere with membrane formation. For instance, a lipid-soluble extract of paprika prevents olive oil from forming stable micelles with egg white glycoproteins. Garlic oil has a similar effect. Phospholipids extracted from soybeans also interfere with the ability of olive oil to form stable lipo-glycoprotein micelles. Flax seed oil disrupts the membranes produced by other triacylglycerols, and appears to precipitate component glycoprotein. Perhaps an abundance of polyunsaturated fatty acid chains interferes with the association of glycoprotein molecules. Lipo-glycoprotein micelles stored in ozonated water tend to break open unless covered by a film of oil.

Lipophilic drugs, diagnostics, flavorings, fragrances, and nutrients can be introduced into the lipid phase during membrane formation. However, some of these substances may interfere with the association of glycoproteins. It is recommended therefore that lipophilic and other substances be introduced into the oil after a stable membrane has been allowed to form.

A patented method was developed to produce stable micelles containing substances such as garlic oil that tend to disrupt micelles (Mullen, 1998.) It involves the preparation of a water-in-oil emulsion of glycoprotein solution in a triglyceride such as olive oil followed by the introduction of a second hydrophobic substance. The emulsion is flipped by the addition of an abundance of glycoprotein solution followed by rapid agitation. A micelle thus prepared has a layer of oil inside the membrane which protects it from the second hydrophobic substance contained with the interior. The inclusion of saturated fats may further stabilize micelles produced by this method.

Liquid hydrocarbons, such as hexane and heptane, have also been found to induce the production of relatively stable glycoprotein micelles. Large vesicles produced from certain glycoproteins, such as those present in liquid egg white, can be lifted from solution on a filter or support. When subjected to a vacuum or to heat, the membranes break and the hydrocarbon evaporates. A thin, brittle film of glycoprotein remains on the substrate.

EXAMPLE I

Inverse Micelles of Egg and Orange Juice Containing Aspirin in Acetic Acid 975 mg aspirin was mixed with warm gelatin made from dissolving 2 packages of Knox unflavored gelatin in 1 cup of simmering distilled water. The gelatin/aspirin mixture was dripped from a pipette into a test tube containing chilled corn oil and refrigerated.

A membrane was formed by layering corn oil over 5 ml of the liquid portion of unfertilized hen egg white to which 30 ml isotonic saline solution had been added. After 15 minutes, the mixture was placed into a pan of water and heated until it had turned white. When the mixture had cooled, it was refrigerated for ½ hour.

The gelatin/aspirin beads were dropped onto the membrane from a pipette. The solution was swirled, causing the beads to break free of the surface membrane and become enclosed within micelles. The entire mixture was poured into a plastic zip-lock bag to which 200 ml distilled water had been added. In order to allow excess fluid and oil-filled micelles to escape, a small slit was cut in the bag above the level at which gelatin/aspirin-filled micelles rested. Then a corner of the bag was cut off, and micelles were allowed to exit into 10 ml acetic acid solution having a pH of 3. One drop of McCormick red dye was added to the acetic acid, and the mixture was allowed to rest at room temperature. The experiment was repeated with the exception that the source of glycoproteins was frozen orange juice, and the membrane formed was not heated. A control of gelatin/aspirin beads prepared in corn oil was swirled in distilled water, then placed in acetic acid containing red dye. One hour later the gelatin beads were removed from the acetic acid solution and examined. Micelles formed from boiled egg white were intact. Clear oil-filled micelles of varied contour and round gelatin-filled micelles were seen among flecks of red-stained precipitated glycoprotein. The gelatin matrix contained evenly spaced, clear inclusions of about 20 microns in diameter. By contrast, the micelles formed in orange juice had swollen in size and were stained darkly around their sharply defined edges. When a micelle was broken by heat from the microscope lamp, clear gelatin was seen pouring from a red membrane. In the control, very few beads were found intact after an hour. Those that were seen had indistinct edges, and had become smaller.

EXAMPLE II

Recovery of Glycoprotein From Aqueous Medium 0.10 ml (one drop) of liquid egg white was dropped into 375 ml distilled water. The mixture was poured into a shallow glass dish measuring 7×11×2 inches. The aqueous solution, which was about ¼" deep, was covered with a thin layer of heptane sprayed from an atomizer. The dish was rocked gently for about 5 minutes. Heptane-filled vesicles of varied shapes began to form beneath the surface after about a minute. The mixture was transferred to a glass cylinder. Vesicles were collected from the surface in a large-mouthed pipette and placed on slides for microscopic examination. Clear, delicate bubbles of heptane ranged in size from 600 microns to 10 microns in diameter. When the heat of the microscope lamp caused a bubble to pop, its persistent wrinkled membrane could be seen shrinking as the heptane evaporated. Long folds indicated that a continuous, transparent membrane lay just above the micelles. When the aqueous solution and heptane had evaporated, roughly circular patches of whitish material were arranged in regular, concentric arrays spaced about 2.5 microns apart.

The aqueous solution from which micelles were removed was placed back into the rectangular dish and sprayed with heptane. No micelles formed when the solution was rocked, indicating that all glycoprotein had been extracted by the initial operation.

EXAMPLE III

Inverse Micelle Containing $CO_2$

Olive oil was used to form a continuous membrane over 20 ml distilled water mixed with the liquid portion of an egg white contained in a plastic cup. The cup was rocked to cover the edges with oil. Carbonated water was poured into the solution. A hole that had formed in the membrane by the introduction of fluid was mended mechanically by pushing edges together with a wooded stick. Carbon dioxide that had escaped into the oil above the membrane appeared as irregular clusters of small beads when viewed at 100×. Bubbles of carbon dioxide rose in the aqueous solution and pushed the membrane upward into the oil layer. Some of these became detached and floated up onto the oil above the membrane. One inverse micelle containing carbon dioxide persisted for eight hours under the heat of the microscope lamp. When it was punctured with a sharpened stick, the carbon dioxide escaped, leaving behind a clear, delicate membrane that persisted in the oil layer.

EXAMPLE IV

Cooked Olive Oil/Egg Micelles Used as a Spread 5 ml liquid egg white was added 30 ml isotonic saline solution. No glycoprotein precipitated. 20 ml olive oil was added and allowed to form a membrane at the surface. The mixture was poured between two cups several times until the membrane had broken into relatively large micelles measuring about 1.5 mm in diameter. Half of the mixture was forced through a nylon filter with pores of 0.4 mm. The two sets of vesicles were cooked until the aqueous solution in which they were suspended had turned white. A sample from each set was viewed at 40×. A large range of sizes existed in both, though the filtered vesicles tended to be smaller, averaging about 2 mm in diameter. Masses of glycoprotein adhered to clumps of micelles in the unfiltered set, but were largely absent in the filtered set. Micelles from each set were lifted from solution in a spoon and spread on toast. When eaten, those from the unfiltered set tasted mildly of olive oil, while those from the filtered set had no perceptible flavor of olive oil, but a pleasant, mild taste and consistency resembling unsalted butter.

EXAMPLE V

Vegetable Dye in Gelatin and Oil

Two packages of Knox unflavored gelatin were dissolved in simmering distilled water. Six drops of McCormick food color were added. The mixture was allowed to reach room temperature at which it remained liquid for several hours.

Yellow oil, decanted from a mixture of ground turmeric and peanut oil, was layered over a mixture of the liquid portion of egg white and distilled water. A membrane formed at the interface between the oil and aqueous solution.

About 15 ml of the liquid gelatin solution was dripped onto the membrane such that each drop was separated by few millimeters of oil. The drops of gelatin caused the membrane to stretch and hang down into the aqueous solution. The mixture was placed in a freezer for about five minutes, until the gelatin had congealed. Then the container was swirled, forcing the gelatin beads to stretch and break free of the surface membrane. A ball of gelatin was lifted from the mixture and placed on a microscope slide. A yellow layer of oil could be seen surrounding the entire pink ball of gelatin. Blue food coloring added to the slide stained the membrane surrounding the oil, but did not color the gelatin. Pressure was applied with a wooden stick to break the membranous envelope. Slowly the blue dye began to stain the gelatin where the membrane was broken.

EXAMPLE VI

Odor of Dead Fish Trapped

A 2" by 2" piece of rotting codfish was rinsed lightly in tap water and placed in a plastic bag containing 15 ml olive oil. The tissue was massaged in the oil through the plastic, then discarded. The remaining oil retained the foul odor of rotting fish. A hole pierced in one corner of the bag was used to drip the oil onto the lipid surface of a membrane formed from about 15 ml olive oil layered over about 25 ml of the fluid portion of egg white. The mixture was then shaken to form micelles. The odor was almost completely masked. A disposable plastic pipette was used to transfer about 10 ml of micelles, along with underlying glycoprotein solution, into a capped glass bottle. The bottle was kept closed at room temperature for several days and opened periodically to determine whether the odor was escaping from the micelles. It did not. Instead, an ester-like, undefined odor, mildly unpleasant, could be detected at the mouth of the bottle. However, after two days, when a few micelles were transferred from the bottle to flexible plastic and mashed, a nauseating odor was detected.

EXAMPLE VII

Liposome-Like Vesicles 30 ml steam distilled water was added to 5 ml liquid egg white in a plastic cup. Denatured proteins that settled to the bottom of the container were removed through a pipette along with about 10 ml of the aqueous solution. 5 ml cold-pressed olive oil was layered on the solution and a membrane was allowed to form. Glycoprotein solution was drawn from beneath the membrane in a pipette. Several drops were placed separately on the oil surface above the membrane. The cup was gently sloshed to cover the drops with oil. Then the mixture was poured between two cups to break up the surface membrane and double-membrane covered vesicles. Immediately, the mixture was transferred into a glass test tube and observed as micelles and liposome-like vesicles rose to the surface. The yellowish oil-filled elements sorted by size, the larger closer to the top of the aqueous solution. Those that contained glycoprotein solution appeared whitish. The largest of these were the size of a pinhead, and appeared clear to the naked eye. They floated at the bottom of the layer in a haze of microscopic oil-filled micelles.

Double-membrane bound vesicles were formed as described above. Excess fluid was drawn off, and micelles were transferred to a small glass bottle. Olive oil was added to the surface, and bottle was capped. Three weeks later, clear double-membrane-bound vesicles one to two mm in diameter could still be seen floating beneath the smaller oil-filled micelles. When observed at 100×, the smooth, rounded contours of bounding vesicles were in sharp contrast to flaccid, wrinkled membranes contained within. Inner vesicles often adhered to outer bounding membranes. Occasionally a small tube could be seen connecting the inner to the outer membrane, forming a channel between the lumen of the inner vesicle and the aqueous environment, through which solution had apparently escaped.

EXAMPLE VIII

Rehydration of Membranes

A pool of micelles from the the preparation described above had remained on a microscope slide for a week. To the naked eye, it appeared to be a coherent mass of small yellow spheres surrounded by yellow oil. Observation at 40× revealed oil-filled membranes adhering to one another in a soap-bubble configuration. When touched with a wooden toothpick, micelles broke into rigid pieces that retained the rounded contours of contiguous bubbles. Oil that had previously been contained within the micelles flowed onto the microscope slide. A drop of distilled water containing blue dye was added to the edge of the yellow mass. Fragments of broken micelles suddenly appeared to dissolve in the water and merge with one another, forming a large continuous, water-filled membrane. Stretch marks resembling those of plastic wrap could clearly be seen in the surface membrane under which began to float the individual oil-filled micelles that had not been broken. One of these was depressed with a fragment of wooden toothpick. Its membrane was flexible, and it did not break, but rather regained a rounded contour when the pressure was released.

EXAMPLE IX

Membrane Boiled in Acid

A lipo-glycoprotein membrane was prepared as described in the example above. The mixture was shaken to form clear vesicles filled with yellowish olive oil. Most of the glycoprotein solution and precipitated proteins were removed by pipette and replaced with 50 ml of sodium biphosphate solution (pH 4). The mixture was transferred to a Pyrex dish and boiled for 5 minutes. The oil-filled vesicles became opaque and many broke open. White precipitate formed in the biphosphate solution. The precipitate and biphosphate solution were removed by pipette and replaced with distilled water. The container was shaken to re-form oil-filled vesicles at the surface. When examined at 40×, rounded micelles that appeared brownish were contained within large, rectangular or pointed vesicles. Adjacent brownish micelles tended to adhere to one another and to the bounding outer membrane. A feathery residue of precipitated protein was seen clinging to small oil droplets that were dispersed throughout the solution surrounding the vesicles. When an aqueous solution of blue dye was added to the preparation, it was possible to determine at 400× that the substance contained within brownish micelles was oil in which were suspended evenly dispersed particles 2.5 microns in diameter or smaller.

It is assumed that boiling removed oligosaccharides from the glycoprotein membranes, allowing the formation of complex vesicles that do not appear when intact glycoproteins and oil are mixed. It is also possible that the inclusions seen within the oil fraction are hydrophobic protein fragments.

It is interesting to note that multiple layers of membranes are also formed when an aqueous solution containing soluble proteins that are not glycosylated is mixed with oil. For instance, human blood serum contains a large proportion of non-glycosylated albumen. When mixed with oil, blood serum has been observed to form vesicles that contain within the oil compartment smaller vesicles that sequester aqueous solutions that, in turn, contain even smaller oil-filled micelles.

EXAMPLE X

Phospholipid Inclusions

A lipo-glycoprotein membrane was prepared as described in the example above. In a separate container, a pea-sized ball of Calbiochem lecithin was mixed with 3 drops of red food color, then stirred into 5 ml olive oil. The lecithin mixture was dripped onto the olive oil above the lipo-glycoprotein membrane. After five minutes the mixture was swirled. After an hour, the preparation was poured into normal saline solution and shaken. Membraneous structures were examined under the microscope. Tiny bright red dots were observed both inside and outside of bounding oil-filled vesicles. Some membranes were stained red. Round, oil-filled vesicles persisted for days at the surface of the solution. The aqueous solution below became pink, indicating that food color had escaped from bounding lipo-glycoprotein vesicles. Eventually bounding vesicles broke open. The membrane that formed at the interface no longer lay flat on the aqueous solution, but swirled up into the oil, indicating a loss of surface tension. It is possible that lecithin displaced the glycoproteins of the original membranes.

400 mg Vita-worth soybean phosphatide complex was dripped onto a membrane prepared as described above from olive oil and an aqueous solution of liquid egg white. The brown phospholipids slowly dissolved in the olive oil and spread out over the membrane. The mixture was shaken into micelles, and red food coloring was added to the aqueous solution. Then the micelles were placed in a ziplock bag and washed with distilled water. When viewed at 100×, many odd-shaped inclusions were seen disbursed throughout the oil. Patches and halos of pink around micellar surfaces indicated that glycoproteins were still present. Micelles appeared milky to the naked eye. Olive oil and soybean phosphatide complex were examined separately at 100× to assure purity. Both lipids were clear and devoid of the inclusions seen within micelles.

EXAMPLE XI

Beer Within Membranes

Beer was forced through a glass pipette into the surface of a flexible membrane formed as in the example above. Vesicles containing beer were examined at 40×. Large oil-filled vesicles floated in a solution that appeared slightly flocculent and brownish under the microscope. Within these were smaller round, clear vesicles containing beer and dark-rimmed bubbles of carbon dioxide gas that clustered together. Tiny droplets of condensate could be observed within some of the gas-filled bubbles.

EXAMPLE XII

Vinegar and Soda

Cornstarch was boiled in water to produce about 50 ml of thin, clear paste. When it was still warm, about 5 ml liquid egg white was mixed into the starch. Vinegar and red food color were added to half of the mixture. Sodium bicarbonate powder and blue food color were added to the other half. In a Pyrex cup, individual drops of each starch mixture were placed in the oil above a membrane prepared as described in the example above. Forced air was applied to break up the vesicles. Then the entire mixture was cooked slowly until the aqueous solution below the membrane had turned white. Gradually, carbon dioxide bubbles rose in the aqueous phase, as a lavender tint appeared, indicating that both vinegar and soda had escaped. A few bluish, soda-containing vesicles remained intact for weeks in the aqueous solution beneath the surface membrane.

EXAMPLE XIII

Gelatin Crystals

A planar membrane was formed by layering about 5 ml olive oil on the surface of a mixture of 30 ml distilled water and the liquid portion of an egg white. Glycoprotein solution was withdrawn from beneath the membrane and dropped onto the oil surface. Inverse membrane-bound vesicles formed and were suspended by the original membrane over the aqueous solution. Then dry Knox unflavored gelatin crystals were added to the oil surface of the original membrane. After a few moments, crystals of gelatin could be seen dropping individually through the membrane. Some remained suspended at the interface, while others sank at the bottom of the container. In the area where gelatin had been added, the membrane lost its ability to suspend fluid withdrawn from the aqueous solution. Red McCormick food coloring was added to the aqueous solution; and the membrane was shaken to form micelles. Microscopic examination revealed tiny, unevenly shaped, rounded crystals suspended in the oil within micelles. In the aqueous compartment, larger, more angular, pink-stained clear crystals of gelatin adhered to the outer surfaces of membranes. Micelles tended to cling to a one another, unlike those formed from glycoproteins alone.

EXAMPLE XIV

Orange Juice Membrane

An overripe orange was cut and gently squeezed into a plastic cup. 5 ml olive oil was layered on the juice. The juice was then removed by pipette replaced with distilled water. When examined at 100× the oil was orange in color and contained tiny, rounded objects. Fresh olive oil was checked for contamination. It was pure light yellow and contained no visible inclusions. The vesicles were transferred to a Pyrex dish. The distilled water was replaced with sodium biphosphate solution, pH 4, and the mixture was boiled for five minutes. The mixture was cooled, agitated, and examined at 100×. Oil-filled vesicles appeared to be electrostatically attracted to one another. Inclusions were larger than before boiling, and the oil seemed lighter in color.

EXAMPLE XX

Olive, Corn, Soy Oil on Lime Juice 20 ml lime juice was filtered through a nylon mesh with openings 1.25 mm. 100 ml distilled water was added. The mixture was allowed to settle for twenty minutes. About 10 ml fluid from the surface was transferred by pipette into each of three plastic cups. 5 ml of olive oil were added to the first, 5 ml of soy oil to the second, and 5 ml of corn oil to the third. Membranes were allowed to form for about five minutes before the preparations were agitated. Vesicles that formed were observed for several days. Those made in corn and soy oils were rounder and more mechanically stable than those in olive oil.

EXAMPLE XXI

Oil and Paprika Extract

Paprika was allowed to stand in olive for several days. Red-stained oil was decanted and introduced onto a solution of water and liquid egg white using the the following three methods:

In the first, 10 ml red-stained olive oil was layered directly on about 25 ml solution.

In the second method, 15 ml corn oil was layered on 25 ml solution, and membrane was allowed to form. Then 10 ml red-stained olive oil was layered on the corn oil.

In the third method, liquid egg white was drizzled slowly into 15 ml corn oil with constant agitation of the mixture until an emulsion had formed. Then 10 ml red-stained olive oil was drizzled into the mixture with agitation. Quickly about 15 ml of glycoprotein solution was poured in the mixture with agitation.

Each preparation was transferred to a plastic Ziplock bag containing about a cup of tap water, and the mixtures were agitated. After an hour, all vesicles made by the first method were broken, and red oil was clinging to the plastic. After six hours, most of those formed by the second method had broken or merged into larger vesicles. About half of the oil was stuck to the plastic bag, and the vesicles could not be shaken into units smaller than $\frac{1}{8}$ inch. By contrast, vesicles at the top of the third preparation had broken open, but an orange-colored mist of small vesicles persisted. Shaking broke the surface membrane into structures about 2 mm in diameter.

It was observed subsequently that other members of the nightshade family, including tomatoes and green bell peppers, contain substances that prevent the formation of stable lipo-glycoprotein micelles.

EXAMPLE XXII

Peppermint Oil

A solution contain 5 ml liquid egg white and 30 ml distilled water was filtered and placed into a shallow dish. Safflower oil was sprayed over the surface in an amount sufficient to form a continuous membrane. Five ml of peppermint oil was then distributed in drops across the entire membrane. the mixture was poured between two cups, then transferred to a Pyrex dish and placed into a pan of boiling water. After the clear micelles and the solution in which they were suspended had turned milky white, the mixture was cooled. Finally, the aqueous solution was replaced with distilled water and a few micelles were lifted from the surface in a spoon. The aroma of peppermint was slightly discernible, but the flavor was not detected until the micelles were mashed between the tongue and roof of the mouth.

EXAMPLE XXIII

Lifting Membrane From Solution

Peanut oil and turmeric were mixed and allowed to rest overnight. A few drops of bright yellow-stained oil were decanted and sprinkled on top of a pink solution containing 5 ml liquid egg white, 30 ml distilled water, and water-soluble McCormick food coloring. A toothpick was used to drag the oil droplets into a pattern. White filter paper was then carefully pressed onto the entire surface of the fluid. The paper was removed and examined. The area that had contacted the aqueous solution was pink. Where the paper had contacted oil, distinct orange swirls reproduced the pattern produced by the toothpick. A drop of turmeric-stained yellow oil was then placed on a corner to of the paper that had not contacted any colored fluid. The paper was then washed in liquid detergent and examined again. The pink color had disappeared. An indistinct, pale yellow dot remained in the corner. However, where a membrane had been present, orange swirls remained distinct and had not bled nor washed out.

EXAMPLE XXIV

Tissue Targeting

ApoC-III, an apolipoprotein that delays uptake by the liver of triglyceride-rich lipoproteins, is added to 10 ml normal saline solution in a sterile glass container. Trastuzumab (Herceptin, Genentech, Inc., South San Francisco, Calif.), a purified recombinant monoclonal antibody that binds to HER2 receptors of breast cancer cells, is added to the mixture. 5 ml of safflower oil is layered on the glycoprotein solution, and a membrane is allowed to form. In an amount corresponding to a dosage of 60 mg per square meter, Doxorubicin, a tumoricidal anthracycline antibody, is added to the safflower oil above the membrane. The mixture is agitated until a suspension of micelles ranging in diameter between five and one micron is produced in the aqueous medium. A syringe is used to withdraw the smaller micelles, avoiding those that rise to the surface of the solution. The micelles are injected intravenously into a patent suffering from metastatic breast cancer tumors that overexpress the growth factor receptor HER2.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention. Thus the expressions "means to . . . " and "means for . . . ", or any method step language, as may be found in the specification above and/or in the claims below, followed by a functional statement, are intended to define and cover whatever structural, physical, chemical or electrical element or structure, or whatever method step, which may now or in the future exist which carries out the recited function, whether or not precisely equivalent to the embodiment or embodiments disclosed in the specification above, i.e., other means or steps for carrying out the same function can be used; and it is intended that such expressions be given their broadest interpretation.

What is claimed is:

1. A micelle comprising a membrane wherein the outer surface of the membrane is a glycoprotein, and the interior of the micelle is hydrophobic, wherein the micelle contains at least one non-polar, hydrophobic liquid in which optional additional substances are dissolved or suspended;

wherein the micelle is prepared by extracting a glycoprotein from a fluid which is a member of the group consisting of egg white and citrus juices in a process comprising:
   a. adding at least one non-polar liquid to the fluid;
   b. allowing a membrane to form at an interface between the fluid and the non-polar solution;
   c. collecting the membrane formed in step (b) on a solid support.

2. The micelle according to claim 1 wherein the glycoprotein is obtained from egg white.

3. The micelle according to claim 1 wherein the glycoprotein is obtained form citrus fruit juices.

4. The micelle according to claim 1 wherein the optional additional substance is selected from the group consisting of drugs, chemotherapeutic agents, targeting agents, fragrances, pesticides, coloring agents, catalyst, reactants, and nutrients.

5. The micelle according to claim 4 wherein the at least one targeting agent is an antibody.

6. The micelle according to claim 1 wherein the additional substances are selected from the group consisting of non-glycosylated proteins, phospholipids, and starch.

7. The micelle according to claim 1 wherein the non-polar, hydrophobic liquid is selected form the group consisting of triacylglycerols, non-polar lipids and hydrocarbons.

8. The micelle according to claim 1 wherein the solid support is a mesh.

9. The micelle according to claim 1 wherein the outer surface of the membrane includes at least one targeting agent.

* * * * *